US011613557B2

(12) United States Patent
Dias et al.

(10) Patent No.: US 11,613,557 B2
(45) Date of Patent: Mar. 28, 2023

(54) TREATMENT OF KERATIN-CONTAINING BIOLOGICAL MATERIALS

(71) Applicant: WOOL RESEARCH ORGANISATION OF NEW ZEALAND INCORPORATED, Christchurch (NZ)

(72) Inventors: Subasinghe Nissanke George Premalal Jayantha Dias, Dunedin (NZ); Alaa El-Din Ahmed Bekhit, Dunedin (NZ); Luxmanan Selvanesan, Dunedin (NZ); Harold Stephen Bernhardt, Dunedin (NZ)

(73) Assignee: Wool Research Organisation of New Zealand Incorporated

( * ) Notice: Subject to any disclaimer, the term of this patent is extended or adjusted under 35 U.S.C. 154(b) by 367 days.

(21) Appl. No.: 16/098,269

(22) PCT Filed: May 2, 2017

(86) PCT No.: PCT/NZ2017/050052
§ 371 (c)(1),
(2) Date: Nov. 1, 2018

(87) PCT Pub. No.: WO2017/192052
PCT Pub. Date: Nov. 9, 2017

(65) Prior Publication Data
US 2019/0144494 A1    May 16, 2019

Related U.S. Application Data

(60) Provisional application No. 62/330,376, filed on May 2, 2016.

(51) Int. Cl.
| | |
|---|---|
| *C07K 1/14* | (2006.01) |
| *A23J 1/10* | (2006.01) |
| *A23J 3/34* | (2006.01) |
| *A23J 3/30* | (2006.01) |
| *A23J 3/32* | (2006.01) |
| *A23L 33/175* | (2016.01) |

(52) U.S. Cl.
CPC ............ *C07K 1/145* (2013.01); *A23J 1/10* (2013.01); *A23J 3/30* (2013.01); *A23J 3/32* (2013.01); *A23J 3/348* (2013.01); *A23L 33/175* (2016.08); *A23V 2002/00* (2013.01)

(58) Field of Classification Search
CPC .... C07K 1/14; C07K 1/145; A23J 1/10; A23J 3/34; A23J 3/30; A23J 3/32; A23J 3/348; A23L 33/175

USPC .......................................................... 426/657
See application file for complete search history.

(56) References Cited

U.S. PATENT DOCUMENTS

| | | | |
|---|---|---|---|
| 2,414,303 A | 1/1947 | Holloway et al. | |
| 4,172,073 A * | 10/1979 | Kadri | C08H 1/06 426/657 |
| 5,049,397 A * | 9/1991 | Koibeck | A23K 20/147 426/7 |
| 5,276,138 A * | 1/1994 | Yamada | C08H 1/06 530/842 |
| 5,849,882 A | 12/1998 | Ping-Fan | |
| 2012/0219667 A1 * | 8/2012 | Kelly | A23J 1/10 426/597 |
| 2016/0333119 A1 * | 11/2016 | Yamazaki | A61K 8/735 |

FOREIGN PATENT DOCUMENTS

| | | |
|---|---|---|
| CN | 1069257 A | 2/1993 |
| CN | 1060625 C | 1/2001 |
| CN | 1757633 A | 4/2006 |
| CN | 103130595 A | 6/2013 |
| EP | 1985647 A1 | 10/2008 |
| EP | 2461680 B1 | 6/2012 |
| GB | 370295 A | 4/1932 |
| TW | 418183 B | 1/2011 |

OTHER PUBLICATIONS

NPL Houqian C et al. CN 104109699 (Oct. 2, 2014, Machine translation) (Year: 2014).*
NPL Fan et al. [English translation of CN 101508782 (A)—Aug. 19, 2009] (Year: 2009).*
NPL McIlvaine buffer (Retrieved on Mar. 22, 2022) (Year: 2022).*
NPL Sheep wool (2015) (Year: 2015).*
NPL Microwave (Retrieved on Mar. 22, 2022). (Year: 2022).*
NPL Google search for NPL sheep wool (Retrieved on Mar. 24, 2022 (Year: 2022).*
NPL Ascorbic acid (Retrieved on Mar. 22, 2022). (Year: 2022).*
International Search Report for PCT/NZ2017/050052, dated Jul. 10, 2017.

(Continued)

*Primary Examiner* — Donald R Spamer
*Assistant Examiner* — Bhaskar Mukhopadhyay
(74) *Attorney, Agent, or Firm* — Crowell & Moring LLP

(57) ABSTRACT

The present invention provides methods for extraction of amino acid-rich fractions from keratin-containing biological materials, and to amino acid-rich protein fractions generated by the methods described herein. The methods involve forming a reaction mixture with keratin containing material at a pH of 1.1 to 6.9. The reaction mixture is exposed to an energy source, such as microwaves, sufficient to degrade the keratin. The amino acid mixture which is subsequently extracted is substantially insoluble.

25 Claims, 6 Drawing Sheets

(56) References Cited

OTHER PUBLICATIONS

Jou et al. "Hydrolytic dissociation of hog-hair by microwave radiation," Bioresource Technology (1999) vol. 70, pp. 111-113.
Yamauchi et al. "Cultivation of fibroblast cells on keratin-coated substrata," Journal of Biomaterials Science, Polymer Edition, 9:3 (1998) pp. 259-270.
Whitbread et al. "Top 10 Foods Highest in Selenium," last updated on Nov. 19, 2016, available at http://www.healthaliciousness.com/articles/foods-high-in-selenium.php.
Office Action for CN Application No. 201780041159.X dated Dec. 5, 2022, 12 pages.

* cited by examiner

TREATMENT OF KERATIN-CONTAINING BIOLOGICAL MATERIALS

CROSS REFERENCE TO RELATED APPLICATIONS

This application is a 371 national phase of PCT/NZ2017/050052, filed May 2, 2017, and claims the benefit under 35 U.S.C. § 119(e) of U.S. Provisional Application No. 62/330,376, filed May 2, 2016, the disclosures of which are incorporated, in their entirety, by this reference.

TECHNICAL FIELD

The present invention relates generally to novel methods for the extraction of amino acid-rich fractions from keratin-containing biological materials, and to amino acid-rich protein fractions generated by the methods described herein.

BACKGROUND OF THE INVENTION

High protein nutrition sources are important for the sports nutrition market as well as for providing a balanced food supplement to undernourished people. Sulfur and its biological derivatives, such as cysteine and glutathione, are very important in influencing the redox balance in the body and influencing cell-based processes and related overall health. Keratin sources, such as wool, feathers, horns and hooves, are very high in protein and in sulfur-containing amino acids, but are typically of low digestibility and nutritional value due to the high degree of cross-linking associated with the disulfide bonds between cysteine residues that occur in keratin proteins.

The Yamauchi method for the dissolution of keratin protein from wool (Yamauchi et al. (1998) *Journal of Biomaterial Science*, Polymer Edition 3:259) involves urea as denaturing agent to disrupt keratin structure, β-mercaptoethanol as reducing agent to break the disulfide bonds, and sodium dodecylsulfate (SDS) as surfactant. However, the nature of the chemical denaturing/reducing agents used does not make this method suitable for commercial production of (in particular) food grade materials.

Another method for producing soluble keratin protein products from wool is described in U.S. Pat. No. 5,276,138. However, it is clear from the teaching of this document that if the pH of the liquid medium is less than 7, the oxidizing agents do not function well, and that high concentrations (>20%) of oxidizing agent are needed. Despite the inventors' assertion that the products could be used as a food additive, these products would not be expected to be palatable to humans, due to the presence of traces of urea in the final product.

A further method for producing soluble keratin protein products from wool is described in EP2461680. This patent describes a nutritional supplement comprising a keratin protein powder made by a process comprising oxidizing a keratin source in a solution with a pH of between 1.5 and 5.0, and through a series of heating and cooling reactions with pH adjustment, generating a keratin protein powder. However, the relative overall conversion rate based on weight of starting material is low.

To address the limitations of prior art methods, the present invention provides improved methodologies involving the treatment of keratin-containing biological materials to yield fractions rich in the sulfur-containing amino acid cysteine (as well as the metabolically-important amino acid arginine) which methodologies yield significantly increased protein conversion efficiencies. Advantageously, these amino acid fractions may be incorporated in nutritional supplements and foods, for consumption by humans and animals.

SUMMARY OF THE INVENTION

The inventions described and claimed herein have many attributes and embodiments including, but not limited to, those set forth or described or referenced in this Summary of the Invention. It is not intended to be all-inclusive and the inventions described and claimed herein are not limited to or by the features or embodiments identified in this Summary of the Invention, which is included for purposes of illustration only and not restriction.

In a first aspect the invention provides a method for extracting an amino acid-rich fraction from a keratin-containing biological material, the method comprising the steps of:

i. providing a reaction mix comprising the keratin-containing biological material and at least one acid, wherein the pH of the reaction mix is between pH 1.1 and 6.9;

ii. exposing the reaction mix to an energy source comprising temperature and pressure for a time sufficient to cause degradation of the keratin-containing biological material in the presence of the at least one acid; and iii. extracting the amino acid-rich fraction from degraded keratin-containing biological material wherein, the amino acid-rich fraction extracted from the keratin-containing biological sample is substantially insoluble.

In another aspect of the present invention there is provided an amino acid-rich fraction obtained from a keratin-containing biological material according to any one of the methods described herein.

In yet another aspect of the present invention there is provided a nutritional supplement or food comprising an amino acid-rich fraction obtained from a keratin-containing biological material according to any one of the methods described herein.

SELECTED DEFINITIONS

Figure 1:
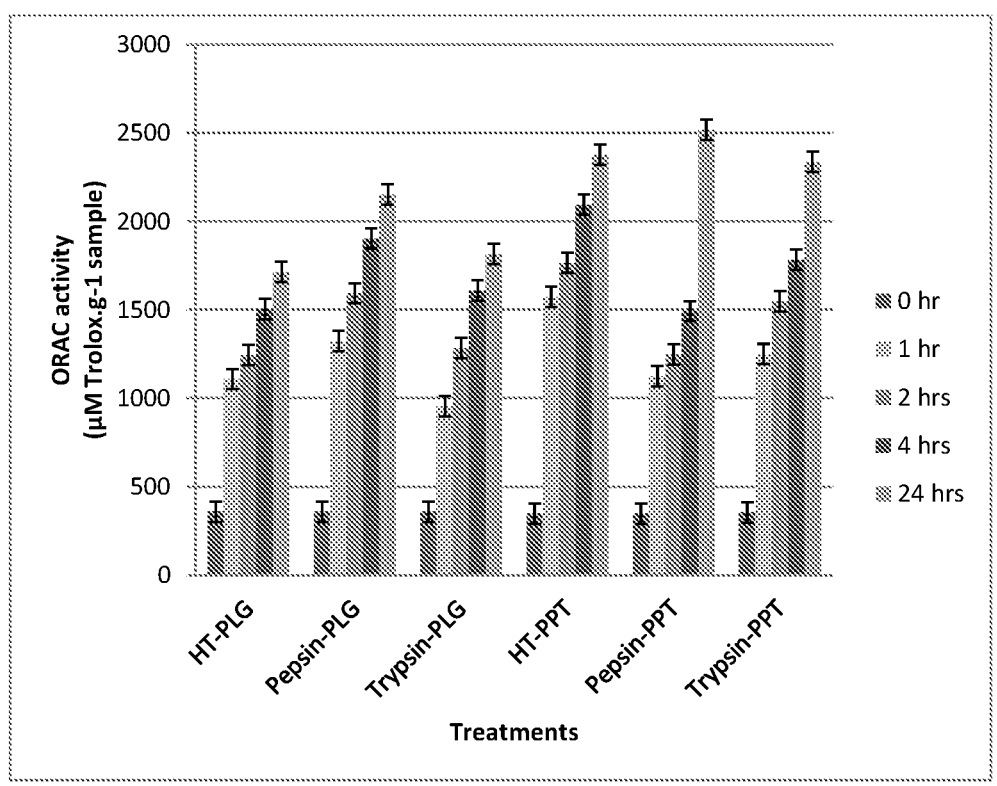
FIG. 1 shows oxygen radical absorbance capacity (ORAC) for HT protease, pepsin and trypsin treated plug and precipitate samples obtained from the treatment of sheep's wool.
Figure 2:
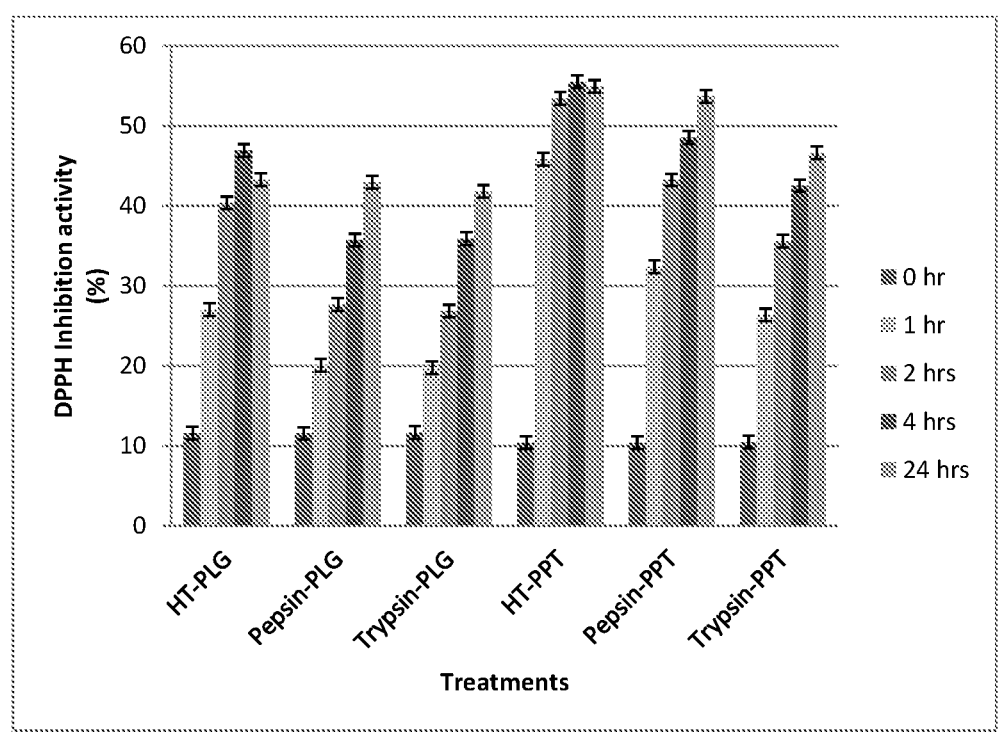
FIG. 2 shows 2,2-diphenyl-1-picrylhydrazyl (DPPH) inhibition activity for HT protease, pepsin and trypsin treated plug and precipitate samples obtained from the treatment of sheep's wool.
Figure 3:
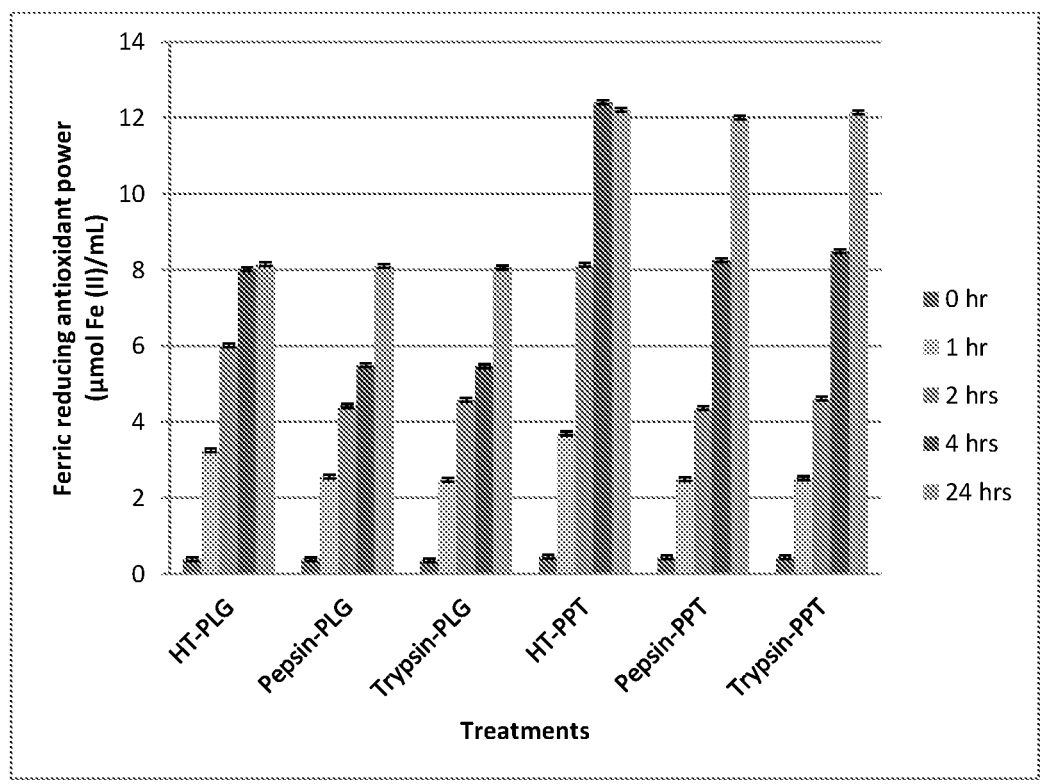
FIG. 3 shows ferric reducing antioxidant power for HT protease, pepsin and trypsin treated plug and precipitate samples obtained from the treatment of sheep's wool.

Unless defined otherwise, all technical and scientific terms used herein have the same meaning as commonly understood to one of ordinary skill in the art to which the inventions belong. Although any assays, methods, devices and materials similar or equivalent to those described herein can be used in the practice or testing of the invention, various assays, methods, devices and materials are now described.

It is intended that reference to a range of numbers disclosed herein (for example 1 to 10) also incorporates reference to all related numbers within that range (for example, 1, 1.1, 2, 3, 3.9, 4, 5, 6, 6.5, 7, 8, 9 and 10) and also any range of rational numbers within that range (for example 2 to 8, 1.5 to 5.5 and 3.1 to 4.7) and, therefore, all sub-ranges of all ranges expressly disclosed herein are expressly disclosed. These are only examples of what is specifically intended and all possible combinations of numerical values between the lowest value and the highest value enumerated are to be considered to be expressly stated in this application in a similar manner.

As used in this specification, the words "comprises", "comprising", and similar words, are not to be interpreted in an exclusive or exhaustive sense. In other words, they are intended to mean "including, but not limited to".

As used in this specification, the terms "keratin-containing biological materials" and "biological materials containing keratin" include any biological material comprising keratin protein. Examples of keratin-containing biological materials include, but are not limited to, wool, horns, hooves, animal hair (including human hair), and feathers.

As used in this specification, the term "amino acid-rich fraction" means the fraction extracted from degradation products generated by the methods according to the present invention, and includes individual amino acids, a peptide or peptide fragment comprising two or more amino acids linked through a peptide bond, as well as full-length/in-tact proteins having a primary, secondary, tertiary and/or quaternary structure.

As used in this specification, the acronym "WDP" means "wool derived protein", being the protein content derived from wool generated by the process and methods according to the present invention. By definition, this includes individual amino acids, peptides, peptide fragments and/or full-length proteins that have been derived from wool.

As used in this specification, the acronym "KDP" means "keratin derived protein", being the amino acid-rich fraction derived from a keratin-containing biological material generated by the process and methods according to the present invention. By definition this includes individual amino acids, peptides, peptide fragments and/or full-length proteins that have been derived from the keratin-containing biological material.

The WDP and KDP generated according to the methods of the present invention may also comprise citric acid, ascorbic acid, and other minerals that were present in the original keratin-containing biological material.

DETAILED DESCRIPTION

Applicants attempted to adapt the Yamauchi method (Yamauchi et al. (1998) *Journal of Biomaterial Science, Polymer Edition* 3:259) in order to reduce urea and SDS levels to within food-safe levels, and replaced β-mercaptoethanol with sodium metabisulfite as reducing agent. However, this approach was met with limited success because overall yields of were low (<30%; data not shown). In addition, there was relatively high amount of urea retained in the extracted protein.

In an attempt to increase overall yield of protein extracted from keratin-containing biological materials, Applicants conceived of an extraction protocol comprising both mechanical and chemical (i.e. food acids) means that achieved increased yield with minimal residual chemical content, making the resultant protein safe for consumption (i.e. food-safe) and palatable. Applicants surprisingly discovered that this extraction process yielded products rich in the sulphur-containing amino acid cysteine, and the metabolically-important amino acid arginine. Refer to (e.g.) Example 14 that lists the amino acid content of the protein/peptide fraction obtained from wool (an example of a keratin-containing biological material).

In certain aspects according to the present invention, Applicants have developed novel methodology for the extraction of amino acid-rich fractions from keratin-containing biological materials, such as (e.g.) wool, feathers etc. The methodology comprises a novel combination of acid and temperature/pressure treatment steps to achieve (i) improved overall yield, (ii) extracted protein containing desired amino acid content and (iii) absence of toxic chemicals in the extracted fraction/product. This is documented in Examples 1-8, and in particular Examples 1-3 (protocol development and optimization), as well as amino acid content profile (Example 14).

Accordingly, in a first aspect of the present invention there is provided a method for extracting an amino acid-rich fraction from a keratin-containing biological material, the method comprising the steps of:
  i. providing a reaction mix comprising the keratin-containing biological material and at least one acid, wherein the pH of the reaction mix is between pH 1.1 and 6.9;
  ii. exposing the reaction mix to an energy source comprising temperature and pressure for a time sufficient to cause degradation of the keratin-containing biological material in the presence of the at least one acid; and
  iii. extracting the amino acid-rich fraction from degraded keratin-containing biological material
  wherein, the amino acid-rich fraction extracted from the keratin-containing biological sample is substantially insoluble.

In an example according to this aspect of the present invention, the energy source comprising temperature and pressure is electromagnetic energy. In a related example, the electromagnetic energy is selected from microwaves and radiofrequency waves. In a further related example, the electromagnetic energy is selected from the group consisting of gas, electricity, fossil fuel, charcoal, or wood fire.

Any electromagnetic wave source such as microwave or radiofrequency wave may be used provided it generates the desired temperature/pressure profile. This is illustrated in the Examples that follow (e.g.) Examples 1-12 use of a benchtop microwave unit (i.e. CEM Microwave Reaction System Mars 6); Example 13 describes use of a prototype microwave apparatus designed and built by the applicants which has a 3 L capacity pressure vessel; and Example 14 describes use of a commercial scale microwave apparatus designed and built by the Applicants which has 30 L capacity pressure vessel. A person skilled in the art will recognise the need to configure the energy output profile of the microwave apparatus to be used in accordance with the methods according to the present invention so as to generate the desired combination of temperature and pressure. This is further illustrated by the data presented in Example 15 in which a comparison of amino acid content obtained from each of the amino acid-rich degradation products (refer below) for the bench-top, 3 L prototype and 30 L semi-industrial scale microwave apparatus is provided. That is to say, irrespective of the microwave apparatus or energy source, provided it is optimised to generate the desired energy output (i.e. temperature and pressure), then the desired amino acid fraction produced according to the methods of the present invention will be very similar.

In other examples according to the present invention, the at least one acid comprises any acid, including but not limited, ascorbic acid, citric acid, acetic acid, benzoic acid, propionic acid, formic acid, sorbic acid, maleic acid and gallic acid. In a related example, the at least one acid is a food grade acid. Examples of food grade acids would be known to persons skilled in the art. In a further related example, the concentration of the acid in the reaction mix is in the range of 1 mM to 8M. For any avoidance of doubt, 1 mM to 8M includes, but it not confined to, 1, 2, 3, 4, 5, 6, 7, 8, 9, 10, 11, 12, 13, 14, 15, 16, 17, 18, 19, 20, 30, 40, 50, 60, 70, 80, 90, 100, 150, 200, 250, 300, 350, 400, 450, 500, 550, 600, 650, 700, 750, 800, 850, 900, 950 mM, 1, 1.1, 1.2, 1.3, 1.4, 1.5, 1.6, 1.7, 1.8, 1.9 and 2.0, 2.1, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9 and 8.0 M acid.

In another example according to this aspect of the present invention, the at least one acid is ascorbic acid. The ascorbic acid may present in the reaction mix at a concentration of between 1 mM and 2 M ascorbic acid. That is, 1, 2, 3, 4, 5, 6, 7, 8, 9, 10, 11, 12, 13, 14, 15, 16, 17, 18, 19, 20, 40, 60, 80, 100, 200, 300, 400, 500, 600, 700, 800, 900 mM and 1, 1.1, 1.2, 1.3, 1.4, 1.5, 1.6, 1.7, 1.8, 1.9 and 2.0 M ascorbic acid. In a particular example, the ascorbic acid is present in the reaction mix at a concentration of about 6 mM.

In another example according to this aspect of the present invention, the at least one acid is citric acid. The citric acid may be present in the reaction mix at a concentration of between 50 mM and 8 M citric acid at 20° C. That is, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 150, 200, 300, 400, 500, 600, 700, 800, 900 mM, and 1, 2, 3, 4, 5, 6, 7 and 8 M citric acid. In a particular example, the citric acid is present in a concentration of about 90 mM.

In yet another example according to this aspect of the present invention, the pH of the reaction mix is between 3.0 and 4.5, that is 3.0, 3.1, 3.2, 3.3, 3.4, 3.5, 3.6, 3.7, 3.8, 3.9, 4.0, 4.1, 4.2, 4.3, 4.4 and 4.5. In a particular example, the pH of the reaction mix is 3.5.

In another example according to this aspect of the present invention, the pH of the acid/temperature/pressure degraded keratin containing biological material is between 2.5 and 3.5. That is, 2.5, 2.6, 2.7, 2.8, 2.9, 3.0, 3.1, 3.2, 3.3, 3.4 and 3.5. In a particular example, the pH of the acid/temperature/pressure degraded keratin containing biological material is 3.3.

In yet a further example according to this aspect of the present invention, the temperature applied by the energy source (e.g. microwave or radiofrequency wave) is applied at between 110° C. and 200° C. That is, 110, 115, 120, 125, 130, 135, 140, 145, 150, 155, 160, 165, 170, 175, 180, 185, 190, 195 and 200° C., as well as integers therebetween depending on the desired energy input. In a particular example, the temperature applied by the energy source is applied at between 160° C. and 180° C. That is, 160, 161, 162, 163, 164, 165, 166, 167, 168, 169, 170, 171, 172, 173, 174, 175, 176, 177, 178, 179 and 180° C.

In a related example, the temperature applied by the energy source is applied using a ramped protocol. The reason for this is to ensure uniform heating of the contents in the reaction mix (vessel(s)) used in the extraction methodology such that the keratin-containing biological material is treated in a way that maximizes conversion efficiency and therefore yield.

In another example according to this aspect of the present invention, the pressure applied by the energy source is applied at between 75 and 220 psi. That is, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124 or 125, 130, 135, 140, 145, 150, 155, 160, 165, 170, 175, 180, 185, 190, 195, 200, 205, 210, 215 and 220 psi.

A person skilled in the art will, based on the teaching provided by this specification, appreciate that the combination of temperature and pressure provided by the energy source (in combination with the acid contained in the reaction mix) is necessary to achieve the desired conversion of keratin protein into amino acid-rich fraction(s). By "amino acid-rich", the fraction may include not only individual amino acids, but amino acids that form part of a peptide or peptide fragment, as well as full-length/intact keratin proteins (with primary, secondary, tertiary and/or quaternary structure).

In another example according to this aspect of the present invention, at least one stabilizing agent is added to the reaction mix following the energy exposure step so as to maintain a reducing environment to prevent repolymerization of keratin protein through reformation of keratin disulfide bonds. This allows the various fractions produced by the methodology according to the present invention (i.e. supernatant, precipitate and/or plug degradation products) to be stored prior to extraction of the amino acid-rich fraction.

An example of a stabilizing agent according to the present invention includes, but is not limited to, ascorbic acid.

It would be apparent to a person skilled in the art that the treatment parameters used in the methods according to the present invention may be varied to yield, for example, (i) amino acid rich fractions that comprise different molecular weight polypeptides and/or proteins (e.g. of low, medium or high molecular weight) depending on their intended utility (e.g. for inclusion in nutritional supplements, food grade products or personal hygiene products, (ii) amino acid rich fractions that under non/reducing conditions either spontaneously repolymerise or remain unpolymerised following treatment (i.e. no disulphide bonds/tertiary structure).

By varying, for example, the type of acid, the acid concentration, the temperature and/or pressure profile, in isolation and/or in combination, the amino acid rich fractions produced by the methods according to the present invention possess different structural characteristics (i.e. size, predisposition to repolymerisation, odour, taste etc)

that make them suitable for inclusion in different products (e.g.) food and/or nutritional supplements, or in personal hygiene products.

In yet another example, the method according to this aspect of the present invention produced discrete degradation products including, but not limited to, supernatant, precipitate and plug. By way of illustration only, refer to Examples 7, 9, 11-14 and 17. A person skilled in the art will be familiar with these terms. Accordingly, the amino acid-rich fraction may be extracted from any one or more of the degradation products, although in a particular example, the amino acid-rich fraction is obtained from the precipitate and/or the plug.

The amino acid rich fractions produced according to the methods of the present invention may be subjected to a wash protocol in order to reduce or eliminate issues associated with undesired odour and/or taste. By way of illustration only, Example 18 describes a wash protocol for keratin derived protein intended for inclusion in personal hygiene products involving a water based wash procedure. By way of further illustration, Example 19 describes a wash protocol for keratin derived protein intended for inclusion in food products or nutritional supplements involving a combination of diluted alcohol and low salt. A person skilled in the art will understand, as a matter of routine, that different wash protocols may be used to reduce or eliminate undesired odour and/or taste depending on the nature of the treatment used.

In yet a further example according to this aspect of the present invention, the keratin-containing biological material includes, but is not limited to wool, horns, hooves, fish processing waste, animal hair including human hair and feathers. In particular examples, the wool is derived from a sheep or goat, and feathers are obtained from a bird such as a chicken (hen).

Advantageously, the amino acid-rich fraction extracted from the keratin-containing biological materials according to the methods of the present invention contain a high percentage of desired amino acids such as arginine and cysteine. In reference to Example 14 (treatment of wool using a 3 L prototype microwave device), the relative cysteine content extracted from the precipitate and plug was 5.9/79.5 (~7.5%) and 11.8/77.8 (~15%) respectively, and the relative arginine content extracted from the precipitate and plug fractions was 8.3/79.5 (~10%) and 6.5/77.8 (~8%), respectively. Cysteine is desired because it is sulphur rich, and arginine is desired because it is metabolically important.

The amino acid-rich fraction extracted from the keratin-containing biological materials according to the methods of the present invention is substantially insoluble. The term "substantially insoluble" is intended to mean that the amino acid-rich fraction is mostly (if not entirely) insoluble. However, a person skilled in the art will recognise, for example, that a fraction comprising individual amino acids may have a small soluble component, hence the term substantially insoluble. That the amino acid-rich fraction is substantially insoluble reduces the likelihood that free cysteine residues will undergo oxidation thereby conferring stability.

The pH of the reaction mix following degradation of the keratin-containing biological material (i.e. post-energy exposure step), is typically in the range of 2.5 to 3.5, and in particular 3.3. Importantly, this means that the amino acid-rich fraction extracted from the degraded keratin-containing biological material has increased shelf-life, palatability and digestibility, as compared to art-known methods for the extraction of keratin-containing protein from biological materials.

Further, the amino acid-rich fraction obtained from the various degradation products importantly possesses antioxidant/free radical scavenging activity, such as oxygen radical absorbance capacity (ORAC), 2,2-diphenyl-1-picrylhydrazyl (DPPH) free radical scavenging activity and ferric reducing anti-oxidant power (FRAP). Refer to Example 16.

Accordingly, in another aspect of the present invention, there is provided an amino acid-rich fraction obtained from a keratin-containing biological material according to any one of the methods described herein.

Finally, the amino acid-rich protein fraction extracted from a keratin-containing biological material may be formulated in a nutritional supplement or provided as an alternative feed stock for both human and animal consumption. Owing to the unique extraction methodology comprising the combination of chemical (e.g. food acid) and physical (temperature and pressure) parameters, the amino acid-rich protein fraction is food-safe and surprisingly palatable, making it a useful alternative feed stock. This is illustrated by the data presented in Example 10 (mouse feeding study) that demonstrated that a diet supplemented with 10% of the amino acid-rich protein and 10% casein protein fraction performed as well as a 20% casein (protein) containing diet in terms of composition and overall animal weight.

Accordingly, in yet another aspect of the present invention there is provided a nutritional supplement or food comprising an amino acid-rich protein fraction obtained from a keratin-containing biological material according to any one of the methods described herein.

Any reference to prior art documents in this specification is not to be considered an admission that such prior art is widely known or forms part of the common general knowledge in the field.

The invention is further described with reference to the following Examples. It will be appreciated that the invention as claimed is not intended to be limited in any way by these Examples.

EXAMPLES

Example 1

Treatment Protocol Development

An initial treatment protocol was trialed/developed via a combination of chemical and physical degradation means using scoured New Zealand sheep wool obtained from Qualityarns Limited (Milton) as a source of a keratin-containing biological material. Surprisingly, Applicants show that the specific combination of food acid treatment and microwave as an energy source, optionally involving temperature ramping to achieve desired temperature outputs depending on the microwave apparatus employed, could achieve the desired degradation of keratin-containing biological materials.

1.1. Microwave Treatment

Applicants trialled microwaves as an energy source to solubilize/degrade wool (as a keratin-containing biological material) using a bench-top analytical CEM Microwave Reaction System Mars 6 to microwave wool in water in wool:water ratio of 1:40, at 150° C./10 min. However, this approach in itself was unsuccessful as the wool morphology remained unchanged.

1.2. Temperature Ramping

In order to mitigate temperature variation between different tubes, Applicants trialled a temperature ramping technique, in which the temperature was increased from room temperature (RT) to 150° C. over a 20 min period, and then held at 150° C. for 10 min. Although the appearance of the wool changed from white to brown, the morphology of the wool fibre under scanning electron microscope (SEM) remain unchanged.

1.3. Inclusion of Acids in Wool Treatment Process (Microwave+Temperature)

Using bench-top analytical CEM Xpress Mars Microwave, Applicants added acids to the wool reaction mix in order to aid in the degradation process as well as prevent production of nephrotoxic LALs. Applicants used a range of mineral and organic acids: hydrochloric acid (HCL; at pH 3.1 and 4.6), acetic acid (at pH 3.1) and sodium acetate (buffered at pH 3 and pH 4.5), sodium citrate (buffered at pH 3 and pH 4.5) and sodium ascorbate (buffered at pH 3 and pH 4.5). The buffering was used to maintain an acidic pH during microwaving. All solutions were used at 0.1 M (except HCl which was used at slightly >0.1 M). The pHs used were chosen in order to be within an acceptable range for food, e.g. orange juice is pH 3.3-4.2. Ascorbic acid was chosen as a reducing agent in addition to its ability to lower pH. The wool:water ratio was 1:40. Three temperature regimes were trialled, each for 10 mins: 150° C., 170° C., and 190° C. Ramping involved heating from RT to the final temperature (i.e. 150° C., 170° C. or 190° C. over) over 10 mins, then holding for 10 mins at the maximum temperature, followed by 40 min cooling to ~40° C. to allow safe opening of tubes.

1.4. Results

Microwaved wool was appraised using both SEM and light microscopy (LM). Wool in ascorbic acid tubes went brown. All 190° C. tubes "smelly". HCl @ 170° C. very smelly (points to $H_2S$). Exclusion criteria: smelly/presence of $H_2S$; dark colour/"burnt"; low degree of disruption of (especially) cuticle layer.

150° C./10 min: very minimal changes; intact cuticle visible in all SEMs.

170° C./10 min: much more substantial changes. HCl (pH 4.6)/sodium acetate (pH 4.5) had only small ball of wool remaining, and residual wool plugs had "jelly-like, felt-like core". Sodium ascorbate (pH 3) had wool plugs that were "brown/felted all way through". SEM also showed wool strands with a felted appearance. Sodium ascorbate (pH 4.5) had "very dark brown ball wool". Sodium citrate (pH 3 and 4.5) gave white cloudy liquid/precipitate (ppt)

190° C./10 min: all tubes smelly (points to $H_2S$). HCl tubes (pH 3.0 and 4.6) gave very cloudy, yellow-white solution with ppt. Sodium citrate (pH 3 and 4.5) gave white, cloudy solutions. Sodium ascorbate pH 3 had the best appearance of all tubes: yellowish colour and small amount of ppt. The remaining wool (plug) had the appearance of meat i.e. non-fibrous. Wool cuticle looked almost completely broken down under SEM. Sodium ascorbate pH 4.5: dark brown solution, lots of ppt. SEM: cuticle less broken down than sodium ascorbate at pH 3. Sodium citrate pH 3 had "yellowish, slight ppt", while sodium citrate pH 4.5 produced a residual wool plug that was non-fibrous and "hard/icy in appearance".

1.5 Final pH Measurements of Solutions Post-Microwave Step

As ascorbic and citric acids are both organic acids with degradation temperatures approximating those temperatures used in the treatment protocol (i.e. 150-190° C.), Applicants measured the final pH of the solutions after microwaving to provide insight as to how much of the acid(s) remained undegraded. Except for one control tube containing unbuffered distilled water, the pH of all tubes (at all three temperatures) had pH<5. In addition, all buffered sodium ascorbate and sodium citrate tubes (at all three temperatures) had final pHs within 0.4 pH units of the initial pH of the reaction mix, e.g. <pH 3.4 and <pH 4.9.

1.6. Conclusions (i) ascorbic acid crucial for wool degradation;
(ii) pH 3 achieves better results than pH 4.5;
(iii) citric acid also breaking down wool, and produces more precipitate than ascorbate;
(iv) combination of ascorbic and citric acids (at lower pH) at 190° C. is preferable Example 2

Treatment Protocol Optimization #1

The wool in all sodium ascorbate tubes went brown, possibly due to the high concentration of ascorbate (0.1 M=100 mM). Therefore, Applicants reduced ascorbate concentration and kept citrate concentration the same, the latter partly in order to maintain low pH. Also it is desirable to reduce ascorbate concentration to reduce cost because ascorbic acid much more expensive than citric acid.

2.1 Use of Unbuffered Ascorbic and Citric Acids

In the previous experiments, lower pH gave better wool degradation. Accordingly, Applicants elected to trial unbuffered ascorbic and citric acids. An advantage is that initial pH of wool-containing solution would be lower; although a possible disadvantage is that the lack of 'buffering' power may lead to rise in pH during microwaving. Oxidation of ascorbic acid appears to be inhibited at lower pH: slower yellowing of 0.1 M sodium ascorbate pH 3 solution bottle which had been left on bench, as compared to the same solution at pH 4.5. Ascorbic acid oxidation may explain brown colour of wool in pH 4.5 sodium ascorbate 190° C. tubes in last experiment.

2.2 Trial Different Concentrations of Unbuffered Ascorbic/Citric Acids

Different concentrations of unbuffered ascorbic/citric acids were then trialled, namely:

1. 100 mM (=0.1 M) citric acid (CA)
2. 1,000 mM (=1 M) CA (pH measured @ pH 1.51)
3. 10 mM ascorbic acid (AA)+900 mM (=0.9 M) CA (pH measured @ pH 1.63)
4. 10 mM AA+90 mM CA
5. 25 mM AA+75 mM CA
6. 50 mM AA+50 mM CA
7. 75 mM AA+25 mM CA
8. 5 mM AA+90 mM CA (190° C./30 min only)
9. 100 mM AA
10. 100 mM sodium ascorbate pH 3.13

2.3 Increase in Microwaving Time

Applicants attempted longer microwaving times in an effort to reduce the maximum temperature: from 190° C. to 170° C./30 min as well as 190° C./30 min (literature decomposition temperatures of ascorbic acid (~190-192° C.) and citric acid (≥1.75° C.)).

2.4 Using minimal temperature ramping

1. Ramp RT->170° C. over 10 min
2. Hold @ 170° C./30 min 2.5 Results

The acid/microwave treatments used in these experiments generated three discrete fractions, namely a supernatant (S/N), precipitate (PPT) and plug (PLG).

The best result overall was achieved with 10 mM ascorbic acid+90 mM citric acid @ 170° C./30 min: wool solid orange, good degradation; solution darker orange colour. Most promising, yellow solution plus wool appeared very broken up. The wool:water ratio was 1:33. In comparison, same concentration of acids @190° C./30 min produced a much darker solution with very little plug, most gone into solution/brown-black colour; dark brown solution; faintly "marmitey" smell.

Almost all concentrations of chemicals @ 190° C./30 min gave dark brown/black solutions which indicates that the wool had over-cooked. Best result was 5 mM AA+90 mM CA which gave a cloudy yellowish brown ppt/solution; ppt more "sludgey"—might go into emulsion with water. After drying, plug for this tube felt "rubbery". Lack of black colour in this tube may be due to lower AA concentration (5 mM). Dark colour possibly due to ascorbic acid oxidation.

2.6 Conclusions 5 mM AA @ 190° C./30 min least brown of 190° C. tubes.

Lower AA concentrations in combination with CA @ 190° C./30 min with no ramping:
1. 1 mM AA+90 mM CA
2. 2.5 mM AA+90 mM CA
3. 5 mM AA+90 mM CA
4. 7.5 mM AA+90 mM CA
5. 1 mM AA+50 mM CA
6. 5 mM AA+50 mM CA
7. 2.5 mM AA+75 mM CA
8. 5 mM AA+75 mM CA These experiments yielded inconsistent results, probably due to differences in microwave heating between tubes: e.g. 1 mM AA+90 mM CA yielded a better colour/light ppt; 2.5 mM AA+90 mM CA yielded a black colour; 5 mM AA+90 mM gave a good result. Precipitate samples of some tubes analyzed by SEM all had similarly amorphous-looking structures.

Example 3

Treatment Protocol Optimization #2

3.1 Repeat of Low AA Concentrations at 190° C./30 Min

Due to inconsistent results of the experiments outlined in Example 2, subsequent experiments were conducted (in triplicate) with three tubes for each condition. Applicants tried range of AA concentrations (all in combination with 90 mM CA): 1 mM AA, 2.5 mM AA, 5 mM AA, 7.5 mM AA, as well as 5 mM AA (with no CA). Appearances very different between triplicate replicates. The best results were observed for 5 mM AA+90 mM CA and 7.5 mM AA+90 mM CA tubes. Based on these data, Applicants selected 6 mM AA+90 mM CA as the reaction mix for microwaving.

Subsequently, 10 mM AA was added after microwaving to liquid (including both supernatant (S/N) and precipitate (PPT) degradation products) and distilled water for storing plugs (PLG) in order to maintain degraded wool protein in a reducing environment, so that the keratin proteins will not repolymerize through reformation of keratin disulfide bonds.

Reaction Mix Recipe

| 90 mM citric acid | 17.293 gm/litre |
|---|---|
| 6 mM ascorbic acid | 1.057 gm/litre | make up to 1 L with Milli-Q water.

Applicants initially used Hansell's food grade citric acid (100 g containers) from supermarket, and scientific grade ascorbic acid.

3.2 Temperature Ramping Protocol+Results

Following inconsistent results between triplicates in last experiment, it was identified that hot tubes may absorb more microwaves, thus increasing temperature disparities. To address this a temperature ramping protocol was employed to increase the temperature of each tube in steps, thereby producing more reproducible temperatures: holding temperature at intermediate temperatures should allow time for all tubes to 'catch up'. The temperature ramping protocol used was as follows:
1. Ramp from RT->100° C. over 5 min.
2. Hold at 100° C. for 5 min.
3. Ramp from 100° C.->150° C. over 5 min.
4. Hold at 150° C. for 5 min.
5. Ramp from 150° C.->190° C. over 5 min.
6. Hold at 190° C. for 30 min.
7. Allow to cool ~40° C.

Applicants then increased amount of wool microwaved from 0.4 gm to 1 gm and increased volume of reaction mix/Mars Xpress tubes from 10 ml to 25 ml, which yielded the same wool:water ratio of 1:25.

Temperature ramping appeared to increase the effective temperature of the process, so Applicants hypothesised that the maximum microwaving temperature could be reduced from 190° C./30 min to 170° C./30 min. Advantageously this also reduced the temperature below decomposition temperature of citric acid as reported in the literature 175° C.). The temperature ramping protocol used was then as follows:
1. Ramp from RT->100° C. over 5 min.
2. Hold at 100° C. for 2 min.
3. Ramp from 100° C.->140° C. over 4 min.
4. Hold at 140° C. for 2 min.
5. Ramp from 140° C.->170° C. over 4 min.
6. Hold at 170° C. for 30 min.
7. Allow to cool ~40° C.

The results observed were again inconsistent. Alternating good tubes with overcooked tubes. Also Applicants observed a number of undercooked tubes, with fibrous wool remaining. Applicants then attempted to extend length of time at maximum temperature (170° C.) from 30 to 40 min. Also, all ramping and holding times extended to 5 min, to try to improve consistency of heating between tubes:
1. Ramp from RT->100° C. over 5 min.
2. Hold at 100° C. for 5 min.
3. Ramp from 100° C.->140° C. over 5 min.
4. Hold at 140° C. for 5 min.
5. Ramp from 140° C.->170° C. over 5 min.
6. Hold at 170° C. for 40 min.
7. Allow to cool ~40° C.

The results employing this modified temperature ramping protocol were positive, with a yellow colour (desired) observed. Some tubes (3-4 tubes) had very large amount of precipitate which Applicants attribute to broken down plugs. One tube had no plug.

The amount of microwaved wool was increased from 1 gm to 1.5 gm. This yielded a wool:water ratio of 1:17 from 1:25, and still resulted in complete conversion of wool into the three degradation products (supernatant, precipitate and plug).

Example 4

Treatment Protocol Optimization #3

4.1 Weighed Wool Microwave Experiment

Applicants then tested microwaved wool samples of known weights at 170° C./40 min using the modified temperature ramping protocol (as set out above), separated into supernatant, precipitate and plug degradation products, and then freeze-dried and weighed, in order to obtain an accurate estimate of conversion of wool->fractions (i.e.) yield. Wool samples averaged 1.250 gm (with a range of 1.198-1.302 gm).

Applicants also tried three different concentrations of citric acid (CA), as the effect of lower CA concentrations had not been fully explored.

| reaction mix | pH initial solution | pH final S/N (av 4 tubes) |
|---|---|---|
| 6 mM AA + 90 mM CA | 2.3 | 4.1 |
| 6 mM AA + 50 mM CA | 2.4 | 4.6 |
| 6 mM AA + 25 mM CA | 2.6 | 4.7 |

10 mM AA was added to the final supernatant and precipitate solution post-microwaving to maintain reducing environment, so the pH of the solutions immediately following microwaving would have been higher than that given above (i.e. the added ascorbic acid would have reduced the pH of the final S/N solution). All concentrations were tested in quadruplicate i.e. 3×4=12 tubes total.

4.2 Results 90 mM CA tubes ok/good; 50 mM CA most tubes good/ok; 25 mM CA these three tubes had great/light colour ("white") but plug noticeably bigger/fibrous. These data therefore suggest that 90 mM CA required for solubilizing the plug.

Microwaved wool+solution was collected into separate supernatant, precipitate and plug tubes for the purpose of amino acid analyses (refer to Example 5, below).

Example 5

Amino Acid Analyses of Microwaved Wool Fractions

Freeze-dried fractions for each of the supernatant, precipitate and plug fractions were prepared and sent to the Nutrition Laboratory @ Massey University, New Zealand for amino acid analysis. This procedure involves overnight hydrolysis of peptide bonds in concentrated HCl to give total amino acid concentrations. Note, these analyses do not indicate whether the amino acids are free amino acids, or amino acids that form part of peptides, protein etc. Performic acid was used to oxidize cystine to cysteine to reduce disulfide bonds; so these analyses also do not give information about the oxidation state of cysteines. Also oxidizes methionine to methionine sulfoxide.

5.1 Results

Amino acids quantified in mg/100 mg (=percentage by weight). Tryptophan estimated from amino acid analysis based on previous analyses of wool derived protein. Each value represents a single sample.

| | S/N | PPT | PLUG |
|---|---|---|---|
| total protein (incl Trp (est.)) (mg/100 mg) | 56.8 | 85.3 | 84.4 |
| cysteine (incl. cystine) | 3.9 | 9.6 | 16.2 |

Precipitate and plug fractions were high in cystine/cysteine (note: keratin protein high in cysteine). Also, Applicants observed a high amount of residual food acids in S/N degradation product.

Example 6

Ionic Conductivity Measurement of Reaction Mix

Since the reaction mix is highly acidic, ionic conductivity was interrogated for the purpose of use in semi-industrial scale microwave apparatus. Analysis was carried out using equipment provided by Department of Chemistry, University of Otago. The ionic conductivity probe was calibrated using a 0.1 N(=0.1 M) KCl solution.

6.1 Results

| Solution composition | Conductivity |
|---|---|
| 6 mM AA +50 mM CA | 2,540 µS/cm |
| 6 mM AA +90 mM CA | 3,050 µS/cm |
| 0.1M (=100 mM) CA | 3,180 µS/cm |
| 1M (=1,000 mM) CA | 7,580 µS/cm |

These data demonstrate that the 6 mM AA+90 mM CA reaction mix has an ionic has ionic conductivity in the order of ~3,000 µS/cm. In comparison, 0.1 M KCl=12,150 µS/cm; sea water ~50,000 µS/cm. The reason for the 6 mM AA+90 mM CA reaction mix having lower conductivity than the equivalent concentration of KCl (0.1 M), is that ascorbic and citric acids are weak acids and so are not completely ionized (=dissociated) in solution, unlike the KCl (salt) which is completely ionized.

Example 7

HPLC Analysis of Citric and Ascorbic Acids in Three Wool-Derived Protein (WDP) Fractions Due to low amino acid/protein recovery from freeze-dried S/N fraction (~56%), Applicants wished to determine how much citric and ascorbic acids were remaining in wool-derived protein fractions. These analyses were performed in the presence of a 0.5% $H_3PO_4$ (phosphoric acid; pH 1.74) buffer system made by adding 0.5 ml concentrated $H_3PO_4$ to 1 litre of purified (Milli-Q) water. Flow rate 1.5 ml/min. Detection @208 nm, which is optimal for citric acid. All samples pre-filtered through 0.45 µm filter before injecting.

Sample preparation: took three individual samples from each of the supernatant, precipitate and plug fractions, which had been previously crushed and sieved. Plugs in particular were large and discrete, and somewhat fibrous in appearance; however, all powders (including plug and supernatant) were passed through a metal sieve using stone pestle and ground to a fine dust. The precipitate fraction was not sieved/crushed, since it was in the form of fine powder and had the appearance of discrete, very small pieces of solid. Supernatant powder had heterogeneous appearance, with patches of different colour, possibly due to presence of white-ish citric acid; so also passed this powder through a sieve. There were significant differences in the relative solubility of all powders associated with the degradation products. The supernatant dissolved completely, with no residual particles, yielding a solution with very little colour. The precipitate yielded a cloudy suspension in purified water, with very small particles sedimenting at the bottom of tube. The suspension possessed a slightly yellow appearance, with a large proportion of the precipitate fraction remaining undissolved. The plug fraction yielded a pale yellow suspension with lots of solid particles that didn't dissolve. Tubes were not vortexed or incubated at room temperature for extraction of acids; therefore values obtained for acids in precipitate and plug fractions constitute lower limits. All solutions filtered through 0.45 µm filter.

7.1 HPLC Data (w/w) %+Results

| WDP fraction | AA | CA | total acids | aas | acids + aas | Diff from 100% |
|---|---|---|---|---|---|---|
| S/N | 4.8 | 30.9 | 35.7 | 56.3 | 92 | 8 |

-continued

| WDP fraction | AA | CA | total acids | aas | acids + aas | Diff from 100% |
|---|---|---|---|---|---|---|
| PPT | 1.3 | 9.3 | 10.6 | 84.9 | 95.5 | 4.5 |
| PLG | 1 | 5.5 | 6.5 | 83.9 | 90.4 | 9.6 |

Estimated amount of ascorbic and citric acids in wool/keratin derived protein fractions. Residual ascorbic acid and citric acid in WDP fractions from 2.5 litres reaction mix: 3.6 g ascorbic acid and 23.7 g citric acid.

The amount of residual acid in combined fractions was also interrogated:

|  | in 2.5 L reaction mix | added to 2.5 L after microwaving | total in WDP fractions |
|---|---|---|---|
| ascorbic acid (AA)/g | 2.6 | 4.4 | 3.6 |
| citric acid (CA)/g | 43.2 | — | 23.7 |

The amounts of residual ascorbic acid and citric acid in the WDP fractions probably represent a lower limit, as incomplete extraction from precipitate and plug fractions (also, some extra ascorbic acid in the plug fraction due to storage of plugs in 10 mM AA). These data suggest that, from the initial reaction mix, 45% citric acid and 100% ascorbic acid has been degraded during microwaving. Residual ascorbic acid is less than the amount added after microwaving, suggesting there has been some degradation of the extra ascorbic acid added after microwaving during subsequent storage of the fractions.

Example 8

Selenium Concentration in Three WDP Fractions

The selenium concentration of the three keratin-derived protein fractions were assessed.

|  | S/N | ppt | plug |
|---|---|---|---|
| selenium (µg/100 g) | 7.4 | 19.5 | 27.4 |

While the amount of selenium is considerably lower than brazil nuts (at 1,917 µg/100 gm, the most selenium-rich food), both precipitate and plug fractions would rank 10th on an internet list of the most selenium-rich foods:
  http://www.healthaliciousness.com/articles/foods-high-in-selenium.php

Example 9

Dry Ashing for Mineral Content Analysis of Three WDP Fractions Obtained from Wool Following HPLC analysis, keratin-derived protein fraction powders from wool were analysed to establish ash/mineral content.

| Fraction | Dry ash (w/w)) |
|---|---|
| S/N | 0.44 |
| ppt | 0.05 |
| plug | 0.14 |

In comparison, literature values for dry ash/mineral content of wool vary from ~0.5 to ~2.3%.

Example 10

28-Day Mouse Feeding Study 10.1 Blending of Three Keratin Derived Protein Fractions for Mouse Feeding Study Applicants used amino acid analysis results to decide the ratio of the three WDP fractions for use in a mouse feeding study. The tryptophan concentration was estimated from previous amino acid analysis results (average @ 0.84 mg tryptophan/100 mg total amino acids, or 0.84% of total protein). Dry ash content of fractions estimated @ ~7%; this may differ between the fractions.

Although it is likely that supernatant fraction has the highest concentration of free amino acids/short peptides, which are presumably more easily digestible, Applicants decided to minimize use of supernatant fraction due to its high concentration of citric acid (~31% by HPLC). Note however, that a small amount of the supernatant fraction was retained in the blend.

Applicants settled on a supernatant:precipitate:plug ratio of 5:55:40. This ratio contains ~9% citric acid. As WDP blend will constitute 50% of total protein in mouse diet, 4.5% of total protein will comprise citric acid (i.e. 4.5 gm of every 100 gm protein). Both experimental and control diets were supplemented with additional methionine. Applicants blend contained 11.9% cysteine/cystine, 8.9% citric acid, and 1.4% ascorbic acid.

10.2 Results from 28 Day Mouse Feeding Study

After 28 days on the WDP/casein (50:50; experimental) and casein (control) diets, the mice were euthanized and samples of their blood plasma removed for analysis by New Zealand Veterinary Pathology Ltd. Ten mice were in the experimental group and ten mice in the control group.

No significant differences between WDP-supplemented and control groups in total protein, albumin, globulin, ALP (alkaline phosphatase), AST (aspartate aminotransferase), bilirubin, HDL, LDL and cholesterol were observed. Also there was no significant difference in the final body weights between the two groups. The amount of casein protein in the diet of the experimental group is below the minimum protein requirement, indicating that the WDP was digestible and able to be utilized by the animals in this group as a protein source. The amount of protein (e.g. total protein, albumin and globulin) in the serum of the mice in the experimental group was the same as the control group (in which 100% of dietary protein is from casein), indicating the protein intake in the experimental group was sufficient. In addition, the weights of the animals and their food intake were the same for both groups.

Example 11

Percentage Protein Recovery in Three Fractions from WDP of Known Weight Microwaved Using Variable Citric Acid Concentrations Wool samples were weighed to three significant figures. WDP fractions were freeze-dried and weighed. The amount of protein in each fraction was calculated based on the amino acid analysis of WDP fractions by Massey University Nutrition Dept, which gives the total percentage (=mg/100 mg) of amino acids (=protein) in each fraction. This number was then used to calculate the percentage protein recovery from the wool samples, assuming that the wool is 100% protein. Wool is generally thought to comprise only 95% protein, so the percentage obtained is an underestimate of the percentage recovery. The figures in the table are averages from 3 or 4 tubes with the same concentration of acids e.g. 6 mM ascorbic acid and 90 mM citric acid.

The results demonstrated that all supernatant and precipitate tubes were the desired colour (i.e. white/yellow). The 6 mM ascorbic acid+25 mM citric acid tubes had the lightest-coloured plugs (3 out of 4 described as "light-ish", "light-coloured" and "v. light").

|  | calculated percentage of total wool weight/% | | | |
| --- | --- | --- | --- | --- |
| — | S/N | ppt | plug | total |
| 6:90 AA:CA | 39 | 31 | 19 | 89 |
| 6:50 AA:CA | 35 | 29 | 28 | 92 |
| 6:25 AA:CA | 29 | 25 | 38 | 92 |

11.1 Total Weights WDP Protein Fractions Produced

Six litres of microwaved wool-containing solution (6 mM AA+90 mM CA) was freeze-dried (2.5 L+3.5 L). All freeze-dried powders were ground into a fine dust using a small domestic coffee grinder. The amount of protein in each fraction was calculated based on the amino acid analyses of WDP fractions performed by Massey University Nutrition Dept, which gives the total percentage (=mg/100 mg) of amino acids (=protein) in each fraction. Total protein in 6 L reaction mix was calculated as ~1.3 g wool/25 ml reaction mix×240 (6 L=6000 ml/25 ml)=~312 g wool total.

11.2 Results

| KDP fraction | weight freeze-dried powder/g | calculated protein/g | percentage of total protein/% |
| --- | --- | --- | --- |
| S/N | 192.05 | 108.6 | 44 |
| ppt | 94.05 | 80 | 32 |
| plug | 71.6 | 60.2 | 24 |
| total | 357.7 | 248.8 | 100 |

248.8 g protein/312 g wool × 100 = ~80% recovery of protein from wool.

248.8 g protein/312 g wool×100=—80% recovery of protein from wool.

Example 12

Protein/SDS PAGE Gels of the Three WDP Fractions

The three WDP fractions were run on SDS-PAGE gels. Two 1 mg aliquots of powder from the three WDP fractions were weighed and carried out using two methods of sample analysis for each fraction: IEF (isoelectric focusing) rehydration buffer (IEF RB), and Bolt 1D-PAGE buffer system.

12.1 IEF RB

100 µl IEF RB was added to 1 mg powder, suspended and soaked for 1 h at room temperature, then 5 µl aliquot loaded on the gel.

12.2 BOLT 1D-PAGE

100 µl BOLT 1D-PAGE sample buffer (including reductant), suspended powder, heated at 90° C./5 min (compared to 70° C./10 min in protocol), then 2 µl and 5 µl aliquots were loaded on the gel.

12.3 Results

1. Soluble material appears mainly from ~3.5 kDa-10/15 kDa.
2. Only visualise solubilized/degraded content on gel. IEF RB does not give better solubilization, and is in fact worse for the plug.
3. Higher proportion of soluble material in supernatant and precipitate lanes. In plug lanes, get smearing from 3.5 kDa->loading well, suggesting high proportion of insoluble/higher molecular weight products.
4. Both buffers contain significant reducing agents (IEF has 50 mM DTT; BOLT 1D-PAGE system reducing agent proprietary).

Example 13

Treatment Protocol Using 3 L Pressure Vessel Capacity Prototype Microwave Apparatus 13.1 Microwave Specifications The 3 L pressure vessel capacity prototype microwave employs three domestic-type 2450 MHz magnetron microwave generators, with individual power supplies feeding into a central 3 L hexagonal pressure vessel. Applicants devised three stub tuners per magnetron to adjust microwave intensity and minimize feedback. However, tuners made of aluminium, and these got pitted by arcing of the microwaves, and progressively fused with the tuner sockets. Accordingly, Applicants replaced with brass tuners in order to optimise functionality.

13.2 Sample Preparation 130 g wool (obtained from NZ Marino, scoured but not Soxhlet-extracted) in 2.30 L microwave reaction mix (wool:water ratio 1:18). The microwave reaction mix contained:

| 90 mM citric acid | 38.47 gm/litre |
| --- | --- |
| 6 mM ascorbic acid | 2.352 gm/litre | made up to 2.225 L with Milli-Q water.

13.3 Microwave Temperature Optimised to 160° C.

The prototype microwave is more efficient; original temperature ramping protocol (i.e. maximum temp. 170° C./40 min used with Mars Xpress analytical bench-top microwave gave "very large dark 'rissole'-like plug"; in the 3 L prototype microwave temperature/time decreased to 170° C./30 min, but wool was still overcooked). The temperature reading on controls were taken from four external thermocouple "rods" which are in contact with the outside of the pressure vessel. Since these rods underestimated the temperature reading by 10° C., the maximum temperature was adjusted to 160° C./30 min on the controls to compensate for this error.

13.4 Reduction in Amount of Wool Microwaved

Using 160° C./30 min treatment protocol, observed small (~2 g) residue of what appeared to be "uncooked" wool, mainly contained within the plug. Applicants reduced amount of wool per cycle from 130 to 120 g, then to 110 g, and finally to 100 g. This eliminated the occurrence of unprocessed wool residue.

13.5 Centrifugation of Liquid Fraction (Containing S/N and Ppt Fractions)

Liquid fraction centrifuged in 1 L bottles @ 1,000 rpm/10 min followed by 4,000 rpm/2 min to pellet and separate the precipitate fraction (centrifuge rotor holds 6×1 L bottles). Microwaved liquid frozen overnight and then thawed. When centrifuged, quantity of precipitate increased significantly. In some cases, precipitate was removed by centrifugation both before and after freeze thawing. Reaction mix (containing citric acid and ascorbic acid) in the absence of wool and without microwaving, was frozen overnight, thawed and then centrifuged to check whether the food acids themselves precipitated during this process. These experiments confirmed that no precipitation occurred in the absence of wool and microwaving.

Microwave step: 160° C. for 30 min and allowed to cool. Maximum pressure of vessel at "160° C." (nominal)=95-96 psi. Equivalent to 6.55 bar (1 bar=14.5 psi). From pressure/temperature graph, 6.55 bar~168° C., so cooking temperature of wool is actually ~170° C.

13.6 Commercial Freeze-Drying

Freeze-drying of ppt and plug WDP fractions produced by the 3 L and 30 L microwave units (refer to Example 14 for 30 L unit) carried out by Back Country Cuisine, Invercargill New Zealand.

13.7 Freeze-Drying Efficiency

Plugs freeze-dried in 24 h; precipitate fraction required a further 12 h (36 h total), because of its higher initial water content. The freeze-drier unit is extremely efficient: final product has very low water activity ($A_w$). The lower the water content, the longer the product shelf-life ($A_w$ water=1). An $A_w$ of >0.91 is typically required for the growth of bacteria, while an $A_w$ of >0.7 is typically required for fungal growth.

| fraction | freeze-drying time/h | water activity/$A_w$ |
| --- | --- | --- |
| plug | 24 | 0.00027 |
| precipitate | 24 | 0.02 |
| precipitate | 36 | 0.002 |

13.8 Amino Acid Analysis

The amino acid content of three degradation products (i.e. supernatant, precipitate and plug) were analyzed by Massey University Nutrition Dept.

Amino acids quantified in mg/100 mg (=percentage by weight). Tryptophan estimated from previous WDP preparations @ 0.8 g/100 g for each of the three fractions. Values represent averages of three tubes (triplicates).

| | S/N | ppt | plug |
| --- | --- | --- | --- |
| total protein (incl Trp (est.)) (mg/100 mg) | 58.6 | 84.8 | 80.7 |
| cysteine (incl. cystine) | 3.5 | 8 | 13.4 |

Example 14

Microwave Based Processing Using 30 L Pressure Vessel Capacity Auckland Semi-Commercial Microwave Apparatus in Microwave NZ Workshop 14.1 Microwave Specifications 30 L microwave uses a single 20 kW 2450 MHz magnetron microwave generator, with a circulator and generator, including a water-cooling system with a flow of 40 L per minute. It features a WG243 aluminium flanged waveguide system, a single WG243 quartz microwave window, and a secondary safety window to protect the generator in case the quartz window should burst.

14.2 Sample Preparation 1.1 kg wool (double-scoured wool obtained from Wool Services International [WSI] but not Soxhlet-extracted) in 26 L distilled water (wool:water ratio 1:24). The microwave reaction mix contained:

| 90 mM citric acid | 431 gm |
| --- | --- |

| 6 mM ascorbic acid | 26.3 gm |
| --- | --- | made up to 26 L with distilled water 14.3 Amino Acid Analysis

Three samples for each of the three fractions (i.e. supernatant, precipitate and plug) were analyzed by Massey University Nutrition Dept.

Amino acids and total protein quantified as (w/w) % (mg/100 mg). Tryptophan (Trp) values were estimated based on previous amino acid analyses of WDP, which included tryptophan. Values are in mg/100 mg (w/w) % and three samples were analyzed for each fraction (i.e. in triplicate).

| Amino acid | Supernatant | Precipitate | Plug |
| --- | --- | --- | --- |
| Aspartic Acid | 4.7 | 2.9 | 1.8 |
| Threonine | 3.2 | 4.3 | 5.2 |
| Serine | 4.1 | 5.4 | 6.2 |
| Glutamic Acid | 10.1 | 12.2 | 8.4 |
| Proline | 3.2 | 4.3 | 7.2 |
| Glycine | 2.6 | 4.1 | 4.2 |
| Alanine | 3 | 3 | 2.9 |
| Valine | 3.7 | 4.8 | 5.3 |
| Isoleucine | 2.2 | 3.3 | 2.7 |
| Leucine | 5.3 | 7.4 | 5.1 |
| Tyrosine | 2.5 | 5.4 | 4.3 |
| Phenylalanine | 1.8 | 3.9 | 2.9 |
| Histidine | 0.6 | 0.7 | 0.5 |
| Lysine | 1.9 | 2.5 | 1.8 |
| Arginine | 6.3 | 8,3 | 6.5 |
| Cysteine | 2.8 | 5.9 | 11.8 |
| Methionine | 0.4 | 0.4 | 0.4 |
| Tryptophan (est.) | 0.5 | 0.7 | 0.6 |
| Total amino acids | 58.9 | 79.5 | 77.8 |

Example 15

Comparison of Amino Acid Compositions in WDP Produced by the Three Microwave Units Amino acids quantified in mg/100 mg (=g/100 g). Tryptophan estimated from previous amino acid analyses of WDP @ 0.8 g/100 g for each of the three fractions. Values represent averages of three tubes (triplicates).

WDP Fraction Cysteine (Cys)/Total Amino Acids (g/100 g)(Including Trp (Est.))

| | S/N | | ppt | | plug | |
| --- | --- | --- | --- | --- | --- | --- |
| | Cys | total | Cys | Total | Cys | Total |
| Analytical microwave | 3.9 | 56.5 | 9.6 | 85.2 | 16.2 | 84.2 |
| Prototype microwave | 3.5 | 59.1 | 8 | 84.7 | 13.4 | 80.5 |
| Commercial microwave | 2.8 | 60.1 | 5.9 | 80.6 | 11.8 | 78.7 |

Analytical microwave (i.e. Examples 1-12), prototype microwave (i.e. Example 13) and commercial microwave (i.e. Example 14).

Fourier Transform Infrared Spectroscopy (FTIR) was performed to identify the presence of free thiol groups (indicative of reduced cysteine residues) in WDP in all three degradation products without hydrolysis. Triplicate samples of the three WDP fractions were measured using FTIR and compared with a sample of whey protein. Small peaks representing thiol groups were seen in the WDP fractions, but not in the case of whey protein, demonstrating that WDP contains higher levels of reduced cysteine residues/free cysteine than whey protein.

Example 16

Antioxidant/Free Radical Scavenging Potential of WDP Fractions

In vitro assays evaluating antioxidant properties/free radical scavenging potential of WDP supernatant, precipitate and plug fractions were performed using three established measures for assessing antioxidant potential following protease treatment:
1. Oxygen radical absorbance capacity (ORAC)
2. 2,2-diphenyl-1-picrylhydrazyl free radical scavenging activity (DPPH)
3. Ferric reducing antioxidant power (FRAP)

16.1 Determination of % Inhibition DPPH in Supernatant Fractions

Six supernatant fractions were each measured in triplicate.
Samples: Supernatant fraction of wool protein 1-6, dissolved in deionised water to the final concentration of 1 mg/mL. The results are as follows:

| | S/N sample# | | | | | |
|---|---|---|---|---|---|---|
| | 1 | 2 | 3 | 4 | 5 | 6 |
| % inhibition DPPH | 19 | 41 | 21 | 57 | 53 | 56 |
| ORAC | 175 | 180 | 216 | 216 | 174 | 196 |

16.2 Determination of % Inhibition DPPH in Protein Hydrolysate from Enzymatic Hydrolysis of KDP Precipitate (PPT) and Plug Fractions by HT Protease at 0, 1, 2, 4, and 24 h Samples: 0.1516 g+20 mL deionised water, pH adjusted to pH 6.5, incubation 45° C., +0.0055 HT protease into the protein suspension.

At time 0, 1, 2, 4, and 24 h, the hydrolysates were collected, heated for 20 min at 90° C., centrifuged @13,000 g for 15 min, supernatants were collected and kept at −4° C. prior to analysis. The results were as follows:

| | time/h | | | | | reaction |
|---|---|---|---|---|---|---|
| | 0 | 1 | 2 | 4 | 24 | mix heated |
| PPT (pellet) 1': | | | | | | |
| % inhibition DPPH | 58 | 72 | 72 | 73 | 70 | 83 |
| ORAC | 719 | 1902 | 1879 | 2054 | 2768 | 799 |
| plug (pellet) 2': | | | | | | |
| % inhibition DPPH | 76 | 79 | 80 | 80 | 80 | 86 |
| ORAC | 596 | 1894 | 2201 | 2288 | 2342 | 238 |

Figure 4:
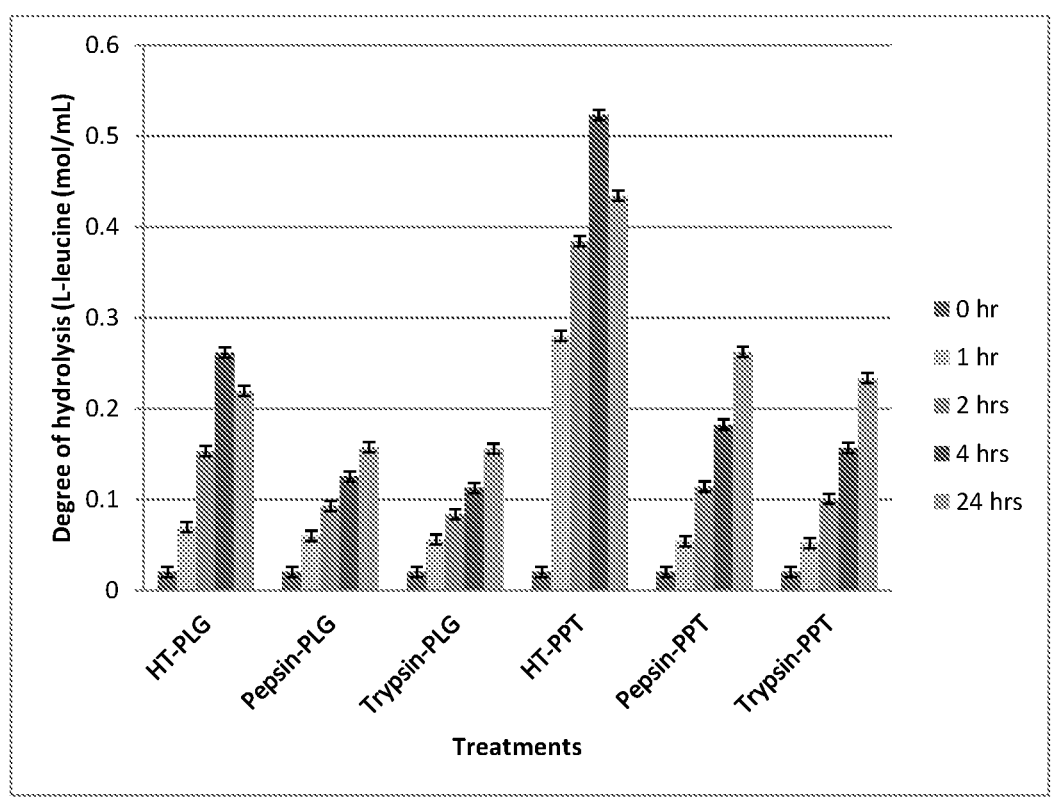
FIG. 4 shows the degree of hydrolysis of L-leucine for HT protease, pepsin and trypsin treated plug and precipitate samples obtained from the treatment of sheep's wool.
Figure 5:
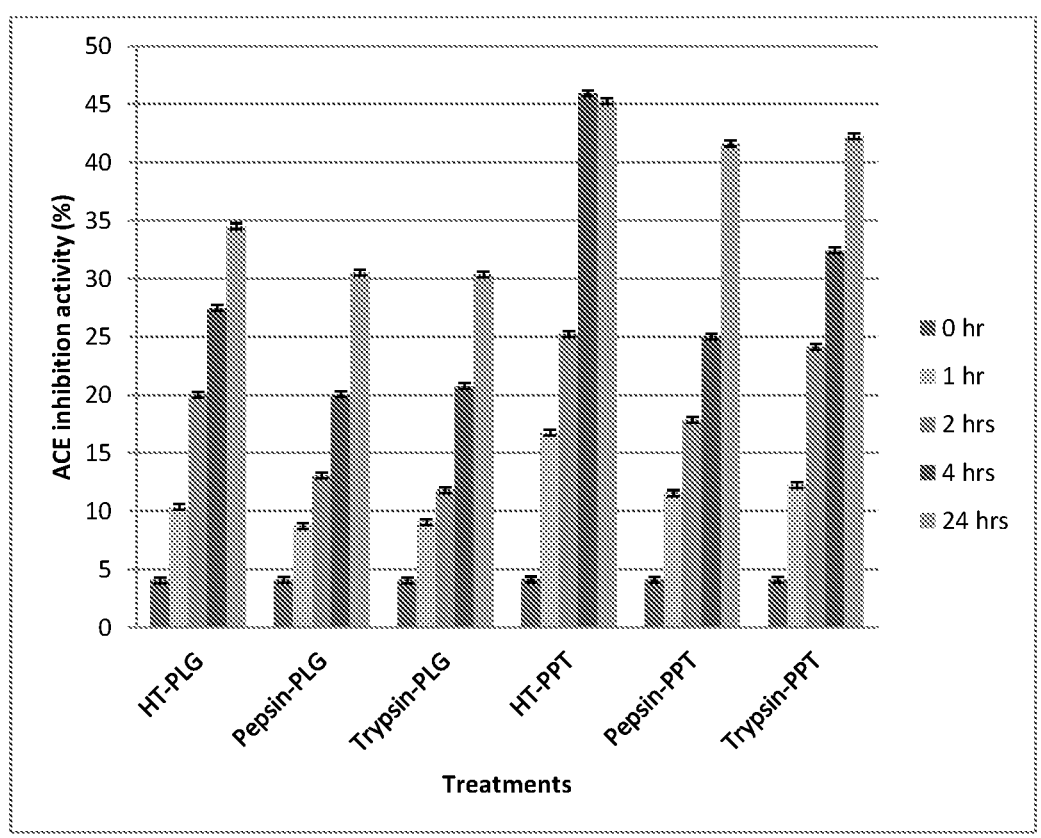
FIG. 5 shows the angiotensin-converting enzyme activity for HT protease, pepsin and trypsin treated plug and precipitate samples obtained from the treatment of sheep's wool.
Figure 6:
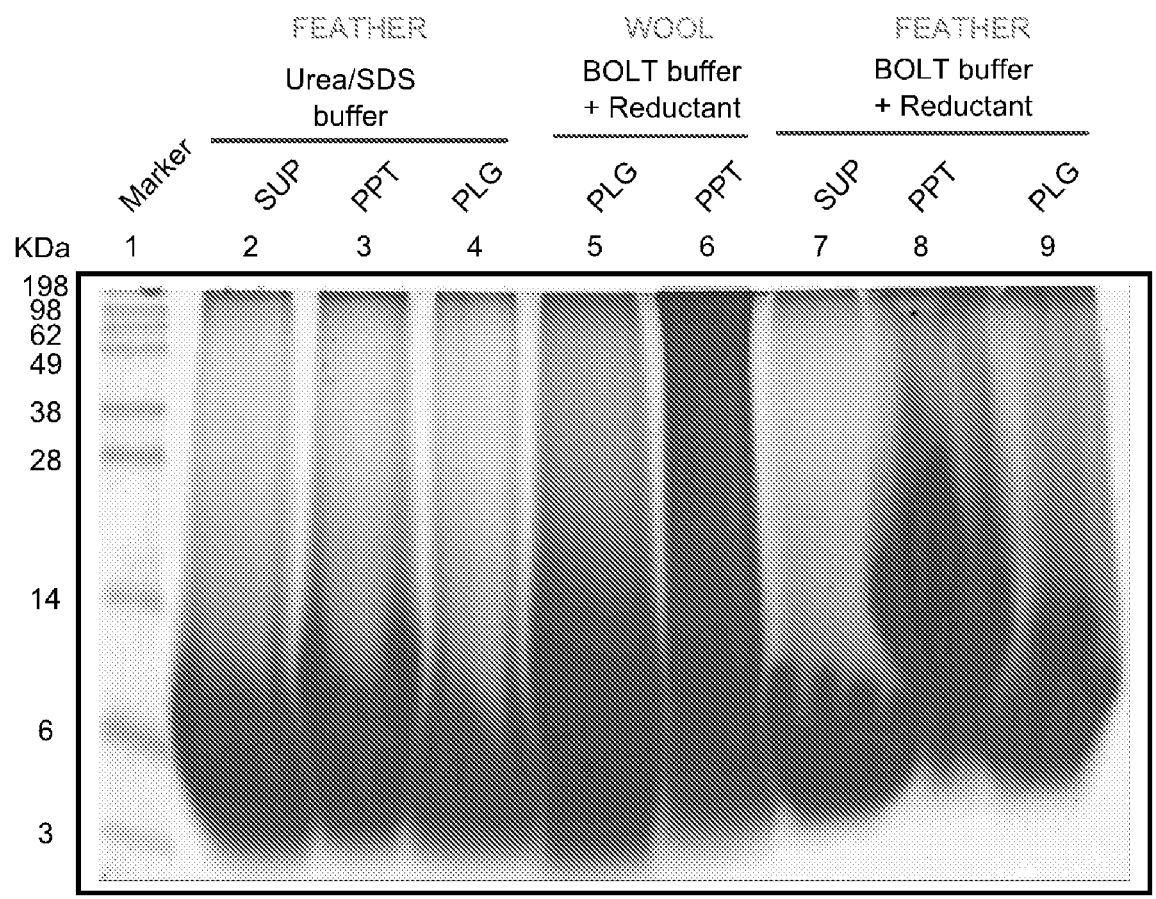
FIG. 6 shows SDS/PAGE protein gels of the amino acid-rich fractions derived from supernatant, precipitate and plug from chicken feathers (lanes 2-4), and BOLT-1D protein gels of the amino acid-rich fractions derived from precipitate and plug from sheep's wool (lanes 5, 6) and supernatant, precipitate and plug from chicken feathers (lanes 7-9).

The results of the antioxidant/free radical scavenging potential studies can be summarised as follows:
1. Generally, the precipitate fraction had higher antioxidant activity compared to the plug.
2. The antioxidant activity was higher with protease HT treatment compared to trypsin and pepsin.
3. The activity was increased with treatment time due to increased hydrolysis of WDP
4. Angiotensin I converting enzyme (ACE) inhibitory activity followed the same pattern as the above antioxidant activity assays (FIG. 4).

16.3 Proximate Analysis (an Index for the Nutritive Value of Foods) of Precipitate (PPT) and Plug (PLG) WDP Fractions

| | Percentage (%) | | | | |
|---|---|---|---|---|---|
| Sample | Moisture | Protein | Ash | Fat | Other |
| 1PPT | 3.54 | 86.15 | 2.91 | 0.04 | 7.36 |
| 1PLG | 3.12 | 86.71 | 2.76 | 0.13 | 7.28 |
| 2PPT | 2.98 | 87.09 | 2.84 | 0.01 | 7.07 |
| 2PLG | 2.98 | 88.03 | 2.86 | 0.12 | 6.02 |
| 3PPT | 2.88 | 86.34 | 2.68 | 0.02 | 8.09 |
| 3PLG | 2.55 | 85.96 | 2.68 | 0.15 | 8.65 |
| Average | | | | | |
| PPT | 3.13 | 86.53 | 2.81 | 0.02 | 7.51 |
| PLG | 2.88 | 86.9 | 2.77 | 0.13 | 7.32 |

In conclusion, WDP is very high in protein, which constitutes 86% of its total weight, on average.

16.4 Trace Mineral Analysis

Trace mineral analysis, using inductively coupled plasma mass spectrometry (ICP-MS) was performed on supernatant, precipitate, and plug fractions. Elemental analysis showed that the toxic heavy metals such as lead, mercury, cadmium and arsenic are within safe levels in all three fractions.

Example 17

Preparation of Keratin Derived Protein from Chicken Feathers 17.1 Chicken Feather Preparation Applicants sourced 10 kg chicken feathers from Brinks Farm, Christchurch, in 10 bags of 1 kg/each. These feathers had been cleaned with bleach solution for disinfection, which would have contributed to the whiteness of the feathers. Applicants cleaned the feathers using a few drops of detergent, and this was repeated six times using fresh water and detergent. After this, the feathers were rinsed to remove the detergent. Feathers were dried in a 75° C. oven for 3 days, and then ground in a food grinder. This chopped up the feathers and quills into small pieces. There was also a small amount of fine powder produced, probably from the quills.

17.2 Microwave Treatment

As the physical structure of chicken feathers appeared to be less robust than wool, Applicants decided to initially trial milder conditions, namely lower microwaving temperatures for a short time.

As with the initial trials with wool, Applicants trialled microwaving using a bench-top analytical CEM Microwave Reaction System Mars 6, with a feather:reaction mix ratio of 1:20, with 1 g feathers added to 20 ml reaction mix.

17.3 Initial Experiments @ 125° C.

125° C./10, 20 or 30 min, with the following temperature ramping protocol:
Ambient->50° C. over 5 min
Hold at 50° C. for 5 min
50° C. —>100° C. over 5 min
Hold at 100° C. for 5 min
100° C. —>125° C. over 5 min
Hold at 125° C. for 10, 20 or 30 min Adopting this protocol Applicants trialled three different concentrations of food acids in the reaction mix plus a negative MQ water-only control (done in triplicate: 3 tubes/ different reaction mix, to give a total of 12 tubes in outermost circle/row of platter):
MQ water control 25 mM citric acid+6 mM ascorbic acid in MQ
50 mM citric acid+6 mM ascorbic acid in MQ
90 mM citric acid+6 mM ascorbic acid in MQ Results The results of this experiments were disappointing, with no degradation of feathers even at the longest microwave duration of 30 min in the 90 mM citric acid/6 mM ascorbic acid tubes. Interestingly, there were localized—usually single—bright yellow dots in a lot of the 10 min tubes, at all food acid concentrations; the reason for this is unknown.

17.4 Initial Experiments @ 170° C.

No degradation was observed at 125° C., accordingly Applicants trialled the same conditions used for wool, with successful results, namely 170° C./10 min.

Ambient->100° C. over 5 min
Hold at 100° C. for 5 min
100° C.->140° C. over 5 min
Hold at 140° C. for 5 min
140° C.->170° C. over 5 min
Hold at 170° C. for 10 min Again Applicants used three different concentrations of food acids in the reaction mix plus a negative MQ water-only control (performed in triplicate: three tubes/different reaction mix, to give a total of 12 tubes in outermost circle/row of platter):

MQ water control
25 mM citric acid+6 mM ascorbic acid in MQ
50 mM citric acid+6 mM ascorbic acid in MQ
90 mM citric acid+6 mM ascorbic acid in MQ Results This experiment was successful, with the best dissolution at 90 mM citric acid/6 mM ascorbic acid, the same concentration of food acids as was found optimal for wool dissolution.

MQ (Control)

No or very minimal dissolution of feathers; in one tube, the solution had darkened slightly to a light brown, reminiscent of the 'burning' seen previously with wool microwaved in distilled water only.

25 mM Citric Acid/6 mM Ascorbic Acid

One tube had reasonable degradation of feathers, with microwave reaction mix turned 'creamy', but very large 'plug' possibly with some featheriness remaining. Other tubes darker brown colour.

50 mM Citric Acid/6 mM Ascorbic Acid

Similar result to 25 mM citric acid tubes. One tube had reasonable degradation of feathers, with microwave reaction mix turned 'creamy', but very large 'plug' possibly with some featheriness remaining. Other tubes darker brown colour.

90 mM Citric/6 mM Ascorbic

Good degradation of feathers. Two tubes had creamy colour, and in the third tube the reaction mix had a brownish colour. All tubes had smallish plug. In all tubes the precipitates and plug fractions occupied ~half of volume of solution. Very similar to wool degradation result, although colour of microwaved feathers perhaps slightly lighter. Smell of microwaved chicken feathers almost identical to that of microwaved wool (due to presence of high levels of sulphur-containing cysteine in keratin). Because this treatment was successful in degrading the feathers, Applicants microwaved a further 12 tubes using the same protocol: 170° C. for 10 min with ramping; 1 g feathers in 20 ml microwave reaction mix of 90 mM citric acid+6 mM ascorbic acid.

All tubes were placed in the fridge overnight, and then the plugs were removed manually and the supernatant and precipitate fractions were separated by centrifugation. Fractions were freeze dried and powderized in coffee grinder, and ~1 ml samples were sent to Massey for amino acid analysis.

17.5 Conclusion

A shorter microwaving period of 10 min at 170° C. using the same reaction mix (90 mM citric acid+6 mM ascorbic acid) was sufficient to degrade the chicken feathers to produce an amino acid-rich powderized fraction almost identical in texture, smell and appearance of the powder, to the amino acid-rich fraction produced using sheep's wool.

Example 18

Wash Protocol—Keratin Derived Protein for Personal Care Products 18.1 Background Keratin Derived Protein (KDP) is largely a mixture of substantially water insoluble peptides and free amino acids that are resultant breakdown products of macromolecular keratin yielded by methods described herein. Since some of these free amino acids and short peptides cause unpleasant odor, taste, and strong orange color of the KDP proving a major hindrance in its consideration as a protein to be used in personal care products. Hence it is essential to eliminate odour and/or taste issues. Applicants therefore developed the following water-based washing method to mitigate the odor, taste, and color of the KDP in a bid to further purify the protein and increase its suitability for personal care applications. Applicants were able to achieve significant levels of purity as a result of repeated washing which diminished the unpleasant odor and taste to a great extent, as well as lighten the color of resultant protein.

18.2 Methodology

The plug and precipitate fractions of KDP were subjected to washing separately, according to the following methodology:

1. 300 g of finely powdered plug and precipitate were each taken separately in 1 L plastic centrifuge bottles (50 g/bottle).
2. 500 mL of distilled water (per 50 g powder) was added to each of the bottles to maintain the powder to water ratio at 1:10.
3. The bottles were shaken well for 2 minutes to encourage maximum dissolution of the soluble components of the plug and precipitate respectively.
4. They were then subjected to centrifugation at 2000 rpm for 10 minutes.
5. Post centrifugation, the supernatant was discarded and the bottles were refilled with fresh distilled water.
6. Steps 3, 4 and 5 were repeated for a total of five times until the plug and the precipitate each went through five washes.
7. At the end of the fifth wash, the supernatant was discarded and the remaining paste was scooped out and spread out evenly onto aluminum foil trays.
8. The foil trays were then covered and subject to freeze-drying for 72 h.
9. At the end of 72 h, the dried plug and precipitate were weighed separately to measure the yield of the final product and was vacuum packed into foil bags.

18.3 Observation

The colors of both plug and precipitate powders in water diminished in intensity from dark brown at the start to pale yellow at the end of the five washes. A similar trend was observed in the odor, which reduced to a great extent. The above changes were an indication that the washing based method was effective in removing the ill effects of the short peptides and free amino acids that contribute to the unpleasant color and odor of the KDP.
18.4 Yield
Plug
Weight of plug prior to washing=300.0 g
Yield after freeze-drying=153.0 g
Precipitate
Weight of precipitate prior to washing=300.0 g
Yield after freeze-drying=169.5 g Example 19

Wash Protocol—Keratin Derived Protein for Food Products
The largely water insoluble keratin derived protein (i.e. amino acid rich fraction) produced according to the methods of the present invention, and intended for application/inclusion in food products was washed using the following protocol in order to reduce or eliminate issues associated with odour and/or taste:
1. A wash solution of 15% ethanol containing 10% NaCl (10 g/100 ml) is prepared.
2. KDP is added at a ratio of 1 part KDP to 9 parts wash (10 g KDP/90 ml NaCl solution).
3. This is mixed until all particulates are suspended in solution, usually 5 minutes.
4. It is left to soak for a minimum of 24 hours.
5. Spun in the centrifuge at 4 degrees, 3000 rpm for 10 minutes.
6. Supernatant is decanted off and Hydrated protein is recovered.

Although the invention has been described by way of example, it should be appreciated that variations and modifications may be made without departing from the scope of the invention as defined in the claims. Furthermore, where known equivalents exist to specific features, such equivalents are incorporated as if specifically referred in this specification.

The invention claimed is:
1. A method for extracting an amino acid-rich fraction from a keratin-containing biological material, the method comprising steps of:
   i. providing a reaction mix comprising the keratin-containing biological material and at least one acid, wherein the pH of the reaction mix is between pH 1.1 and 6.9;
   ii. exposing the reaction mix to an energy source to apply a temperature between 110° C. and 200° C. and a pressure between 75 and 220 psi for a time sufficient to cause degradation of the keratin-containing biological material in the presence of the at least one acid to extract an amino acid-rich fraction, wherein the at least one acid is selected from ascorbic acid, citric acid, acetic acid, benzoic acid, propionic acid, formic acid, sorbic acid, maleic acid and qallic acid; and
   iii. extracting the amino acid-rich fraction from degraded keratin-containing biological material
   wherein, the amino acid-rich fraction extracted from the keratin-containing biological sample is substantially insoluble.
2. The method according to claim 1, wherein the energy source is an electromagnetic energy source.
3. The method according to claim 1, wherein the at least one acid is present in the reaction mix at a concentration of 1 mM to 8M.
4. The method according to claim 1, wherein the at least one acid in the reaction mix is ascorbic acid.
5. The method according to claim 4, wherein ascorbic acid is present in the reaction mix at a concentration of between 1 mM and 2 M.
6. The method according to claim 1, wherein the at least one acid in the reaction mix is citric acid.
7. The method according to claim 6, wherein citric acid is present in the reaction mix at a concentration of between 50 mM and 8 M at 20° C.
8. The method according to claim 1, wherein the at least one acid in the reaction mix comprises ascorbic acid and citric acid.
9. The method according to claim 1, wherein the pH of the reaction mix before exposure to the energy source is between pH 1.1 and 6.9.
10. The method according to claim 1, wherein the temperature is applied in a ramped temperature protocol.
11. The method according to claim 1, wherein the amino acid rich fraction comprises low molecular weight polypeptides or proteins, medium molecular weight polypeptides or proteins, high molecular weight polypeptides or proteins, or any combination thereof.
12. The method according to claim 1, wherein following treatment the amino acid rich fraction repolymerises.
13. The method according to claim 1, wherein following treatment, a stabilizing agent is added to the reaction mix to maintain a reducing environment to prevent repolymerization of keratin protein through reformation of keratin disulfide bonds.
14. The method according to claim 1, wherein the keratin-containing biological material is selected from the group consisting of wool, horns, hooves, animal hair, feathers, fish processing waste, and human hair.
15. An amino acid-rich fraction obtained according to a method comprising:
   i. providing a reaction mix comprising the keratin-containing biological material and at least one acid, wherein the pH of the reaction mix is between pH 1.1 and 6.9;
   ii. exposing the reaction mix to an energy source to apply a temperature between 110° C. and 200° C. and a pressure between 75 and 220 psi for a time sufficient to cause degradation of the keratin-containing biological material in the presence of the at least one acid to generate a substantially insoluble amino acid-rich fraction, wherein the at least one acid is selected from the group consisting of ascorbic acid, citric acid, acetic acid, benzoic acid, propionic acid, formic acid, sorbic acid, maleic acid and qallic acid; and
   iii. extracting the amino acid-rich fraction from degraded keratin-containing biological material.
16. The amino acid-rich fraction according to claim 15, wherein the amino acid rich fraction is water insoluble.
17. The method according to claim 1, wherein the keratin-containing biological material is wool.
18. The method according to claim 1, wherein the wool is sheep's wool.
19. The method according to claim 1, wherein the pH of the reaction mix after exposure to the energy source is between pH 3.0 and 6.0.
20. The method according to claim 1, wherein the amino acid-rich fraction has a reduced likelihood to undergo oxidation.
21. The method according to claim 20, wherein the amino-rich fraction comprises cysteine.
22. The method according to claim 1, wherein a reducing environment is maintained during steps (i)-(iii).

23. The amino acid-rich fraction according to claim 15, wherein the amino acid-rich fraction has a reduced likelihood to undergo oxidation.

24. The amino acid-rich fraction according to claim 23, wherein the amino-rich fraction comprises cysteine.

25. The amino acid-rich fraction according to claim 15, wherein a reducing environment is maintained during steps (i)-(iii).

* * * * *